(12) United States Patent
Farooqi et al.

(10) Patent No.: US 6,368,639 B1
(45) Date of Patent: Apr. 9, 2002

(54) HERBAL SKIN CARE FORMULATION AND A PROCESS FOR THE PREPARATION THEREOF

(75) Inventors: Alaul Hasan Abad Farooqi; Srikant Sharma; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,515

(22) Filed: Mar. 24, 2000

(51) Int. Cl.[7] .................. A01N 65/00; A61K 35/78; A61K 39/385; A61K 31/74; A61K 35/64

(52) U.S. Cl. ................. 424/725; 424/78.02; 424/78.03; 424/539; 424/744; 424/773; 424/774; 424/778; 424/779

(58) Field of Search ............................... 424/725, 78.02, 424/78.03, 744, 774, 778, 779, 773, 539, 195.1

Primary Examiner—Christopher R. Tate
Assistant Examiner—Michele Flood
(74) Attorney, Agent, or Firm—Darby & Darby

(57) ABSTRACT

The invention relates to a herbal skin care formulation comprising of beeswax, stearic acid, glycerol monostearate, olive oil, aloe gel, glycerine, triethanolamine, parabens, propylene glycol, essential oils, sandalwood oil, and the balance comprising rose water. The invention also relates to a process for the preparation of the formulation.

13 Claims, No Drawings

HERBAL SKIN CARE FORMULATION AND A PROCESS FOR THE PREPARATION THEREOF

FIELD OF THE INVENTION

The present invention relates to a novel herbal skin care formulation and a process for the preparation thereof. More particularly, the present invention relates to a natural herbal skin care formulation in the form of a cream.

The formulation is useful to clean and restore skin of the individual user by providing a formulation using aloe gel and essential oils to repair damage and promote supple skin. The invention also relates to a cream formulation which may provide temporary relief of minor pain and in particular, dryness of skin.

BACKGROUND OF THE INVENTION

Everyone has faced the discomfort of dry, chapped hands at one time or another. Not only hands but other external portions of the body particularly foot are susceptible to dryness, irritation and lesions. Over the years, many different compounds and formulations have been used for cleaning and restoring skin. A variety of skin creams and lotions are used to soften skin, repair lesions, combat dryness and reduce roughness in irritated skin. There are also a variety of creams or ointments that are used to reduce the itch from insect bites. Prior art formulations however either act as moisturizers to soften the skin or provide healing for skin lesions and skin cracks.

Also most of the prior art skin care formulations also include ingredients that are not always eco-friendly and are therefore economically unviable. Some of the prior art formulations also contain components that are ultimately harmful to the skin.

Increasingly, the use of natural products for manufacture of skin care products is becoming common. Skin repair products having soaps, detergents, plant extracts and the like are commonly used in this field.

In the art, *Aloe vera* is known to yield a gel which cleans and softens skin (U.S. Pat. Nos. 5,882,666; 5,874,094). Aloe gel has been used as it is a moisturizing agent and antibacterial, antifungal and even antiviral properties of the gel has been demonstrated. Aloe gel polysacchrides have immunomodulatory properties. It is very useful for burns (T. Reynolds and A. C. Dweck, J. Ethnopharmacology 68, 1999, 3–37).

In the prior art, several naturally occurring essential oils are known to act as cooling agents and to have excellent sedative effect. For example, rose water obtained when rose oil is extracted from flowers of *Rosa damascena* by steam distillation has been used as a cooling agent during summer. Rose water is also known to be sedative and calming and is used for palpitation and related problems in Indian systems of medicines (Clare Maxwell-Hudson's Aromathrapy massage book, 1994).

Sandalwood oil obtained from the wood of sandalwood tree, is known for balancing the skin, and for calming sensitive, dry or dehydrated skin. The oil is beneficial also for acne, eczema and chapped, dry skin. Sandalwood is also used in religious ceremonies and plays a key role in Indian Ayurvedic medicines. It is widely used in perfumery for its base note and classic oriental scent and is known to calm and cool the body (The Wealth of India—Raw Materials, 1994).

Vetiver oil extracted from the roots of vetiver grass by steam distillation is known in the art as being sedative, calming and antiseptic. It is used in massage blends and for acne. It is cultivated in India. (A. H. A. Farooqi and Sushil Kumar 1998, Proceedings of $2^{nd}$ Australian Aromatherapy Conference, Sydney pp.1–13).

Germanium oil extracted by steam distillation of the whole germanium plant is known as an anti-depressant and an excellent relaxant for those suffering from nervous tension. The oil is rich in gentle alcohols, geraniol and linalool. It is suitable for all skin and good for acne treatments due to its anti-microbial effect. (Clare Maxwell-Hudson's "Aromatherapy Massage Book", Dorling Kindersley, 1994).

OBJECTS OF THE INVENTION

It is the main object of the invention to provide a natural herbal based skin formulation for skin care.

It is another object of the present invention to provide a herbal based skin formulation that is ecofriendly and is economically viable.

It is another object of the invention to provide a herbal skin care formulation that not only moisturises and softens the skin but also helps in healing of skin lesions and skin cracks.

It is another object of the invention to provide a herbal skin care formulation that does not contain any components ultimately harmful to the skin.

It is an object of this invention to provide skin care compounds, which avoid the disadvantages of previous skin care products.

It is a further object of the invention to provide a skin care formulation that is effective and easy to use.

Another object of the invention is to provide a good cream that can give effective protection to skin and free from any toxicity or toxic residue and irritation when regularly used and should also be cosmetically acceptable having pleasant odour and should not produce side effects.

SUMMARY OF THE INVENTION

The present invention relates to a herbal cream formulation for skin care. Since the components in the formulation are from herbal source, it is very safe and ecofriendly and do not produce any adverse effect. The herbal skin care compound of the invention helps in revitalizing the skin and keeping skin smooth, supple and soft, protecting skin from environmental pollution, minimizing the effects of sunburn and chapping and reducing the effects of dryness.

Accordingly, the present invention relates to a herbal skin care formulation comprising up to five percent of beeswax, up to four percent of stearic acid, up to seven percent of glycerol monostearate, up to thirty percent of olive oil, up to twelve percent of aloe gel, up to eighteen percent glycerine, up to two percent of triethanolamine, up to 0.2 percent of methyl paraben, up to 0.2 percent of propyl paraben, up to eight percent of propylene glycol, up to one percent of vetiver essential oil, up to one percent of geranium oil, up to one percent of sandalwood oil, and the balance comprising rose water with one or more conventional ingredients to complete the compound, wherein the constituents are present in weight %.

The skin care formulation of the invention is not a mere aggregate of the properties of the individual ingredients but is a synergistic composition showing surprising and unexpected properties in skin care and healing of skin cracks and skin lesions.

In one embodiment of the invention, the natural herbal formulation comprises beeswax, stearic acid, glycerol monostearate, olive oil, *Aloe vera* gel, rose water, glycerine, triethanolamine, propylene glycol, geranium oil, sandalwood oil, vetiver oil, methyl paraben and propyl paraben in amounts of 4.4–5%; 3.5–4%; 6.5–7%; 20–25%; 11–12%; 20–25% 14–18%; 1.5–2%; 6–8%; 0.5–1%; 0.5–1%; 0.5–1%; 0.15–0.2% and 0.15–0.2% respectively, wherein the said constituents are expressed in terms of weight %.

In another embodiment of the invention, *Aloe vera* gel may be procured from flowers, leaves and stems.

In another embodiment of the invention, the sandalwood oil used is extracted from sandalwood heartwood or soft wood.

In another embodiment of the invention, vetiver oil used is extracted from roots of the plants.

In another embodiment of the invention, geranium oil is extracted from leaves of the plant.

In yet another embodiment of the invention, rose water is obtained from distillation of rose flowers.

In another embodiment of the invention, beeswax, stearic acid and glycerol monostearate form the cream base for the formulation.

In another embodiment of the invention, the olive oil is extracted from olive berries.

The invention also relates to a process for the preparation of a herbal skin care formulation comprising up to five percent of beeswax, up to four percent of stearic acid, up to seven percent of glycerol monostearate, up to thirty percent of olive oil, up to twelve percent of aloe gel, up to eighteen percent glycerine, up to two percent of triethanolamine, up to 0.2 percent of methyl paraben, up to 0.2 percent of propyl paraben, up to eight percent of propylene glycol, up to one percent of vetiver essential oil, up to one percent of geranium oil, up to one percent of sandalwood oil, and the balance comprising rose water with one or more conventional ingredients to complete the compound, the constituents present in weight %, said process comprising forming an aqueous phase by blending aloe gel with rose water and tan emulsifier, preparing an oil phase comprising beeswax, stearic acid and glycerol by any known method, introducing the aqueous phase into the oil phase under stirring in any conventional manner, and then allowing the mixture to cool, dissolving the essential oils in propylene glycol and then adding the solution of essential oils to the cream while stirring.

DETAILED DESCRIPTION OF THE INVENTION

The main skin problems include acne/pimples, dryness and psoriasis, etc. Proper skin care is necessary for treating these problems. The natural herbal products are in demand for use to control skin problems. The natural herbs are harmless as they don't have side effects. They also have low mammalian toxicity and can be handled safely. The plants used in this formulation are very useful in skin problems.

The formulation of present invention consists of a mixture of glycerine, olive oil, *Aloe vera,* glycerol monostearate, stearic acid, propylene glycol, methyl paraben, propyl paraben, triethanolamine, beewax, essential oils and rose water.

A combination of *Aloe vera* with essential oils in cream base can be used as a good household herbal cream, which results in the protection of skin from different diseases.

The use of essential oils in the present invention employs the belief that a patient must be treated holistically. Essences work organically and can replace the use of tranquilizers. Unlike the modern sleeping pills, essences are not mere sedatives. Most of them are very pleasant to smell providing uplifting effect. Essential oils are employed in aromatherapy, in the appropriate doses, are harmless to the organism and do not cause troubles like those produced by the ordinary psychological drugs.

Rose water is also used in the preparation of the herbal cream of the invention. Rose water is obtained when rose oil is extracted from flowers of *Rosa damascena* by steam distillation and has traces of components of rose oil. Rose water is known in the art as a cooling agent during summer. Rose water is sedative and calming and is commonly used for used for palpitation and related problems in Indian systems of medicines. A rose water compress is known to signs of stress in the face by relieving headaches, eye strain and inflammation (Clare Maxwell-Hudson's Aromathrapy massage book 1994).

In the formulation, sandalwood oil is also used as it is the perfect oil for balancing the skin, and to calm sensitive, dry or dehydrated skin. The oil is beneficial also for acne, eczema and chapped, dry skin. Sandalwood oil is obtained from the wood of sandalwood tree. Sandalwood plants are found in South India, where 70% of the world's supply is grown. The heartwood of the tree trunk is used and the oil is extracted from it by steam distillation. Sandalwood is used in religious ceremonies and plays a key role in Indian Ayurvedic medicines. It is widely used in perfumery for its base note and classic oriental scent. Sandalwood is used to calm and cool the body. It is sedative and used in massage blends to treat anxiety and depression. It is popular in products for its sweet and long-lasting fragrance (The Wealth of India—Raw Materials, 1994).

Vetiver oil was used as it is sedative, calming and antiseptic. It is used in massage blends and for acne. Vetiver oil is extracted from the roots of vetiver grass by steam distillation. It is cultivated in India. (A. H. A. Farooqi and Sushil Kumar 1998, Proceedings of $2^{nd}$ Australian Aromatherapy Conference, Sydney pp.1–13).

The scent of geranium oil resembles rose, with which it shares many constituents. Geranium oil is extracted by steam distillation of the whole plant. The oil is antidepressant. It is an excellent relaxant for those suffering from nervous tension. The oil is rich in gentle alcohols, geraniol and linalool. It is suitable for all skin and good for acne treatments due to its anti-microbial effect. (Clare Maxwell-Hudson's "Aromatherapy Massage Book", Dorling Kindersley, 1994).

Olive oil was used as it has soothing, softening properties. It contains more unsaturated fatty acid than saturated fatty acids. The oil is extracted from olive berries. The oil was part of oil phase of cream base. Stearic acid was used as it is a fatty acid and it was part of oil phase of the cream. Beewax and glycerol monostearate were also used as part of oil phase of cream base. Glycerine, propylene glycol are forms of glycerol which is colourless liquid that absorbs moisture and is used in the manufacture of creams as aqueous phase.

The parabens (methyl and propyl) were used in the preparation of formulation as these compounds are esters of para-hydroxybenzoic acid and have been shown to be effective antimicrobial agents, as well as, being effective against molds and yeasts.

The herbal cream formulation is useful for dry skin, revitalizing the skin and keeping skin smooth, supple and soft, cuts, burns and acne. The composition of the formulation is new, very safe, eco-friendly and does not produce any harmful effects. The combination of aromatic herb used in this formulation have not been used in other creams so far to the applicants knowledge.

The components in the formulation are from herbal source and are very safe and ecofriendly. The ingredients of the formulation of the invention do not produce any adverse effect on the skin. The *Aloe vera* gel is useful for dryness, rose water which is sedative, sandalwood oil which is antiseptic, vetiver oil which is calming and geranium oil which is calming. Olive oil has been used as it is very useful for skin. Beeswax, stearic acid, glycerol monostearate were used to provide cream base. Glycerine was used as source of glycerol. Triethanolamine was used as emulsifier. Methyl and propyl paraben were used as fixative due to antimicrobial properties.

The formulation of the invention shown surprising and unexpected results in treatment of skin lesions and skin cracks as well as in the restoration ans repair of the skin and in cleansing ans softening of the skin. The formulation of the invention is particularly effective in treatment of dryness of skin, sunburn, dark circles around the eyes/dark patches on the face, protecting skin from environmental pollution, revitalizing the skin and keeping skin smooth, supple and soft.

*Aloe gel* is first extracted from the leaves and blended with rose water and emulsifier triethanolamine. This comprises aqueous phase of the cream. For preparation of cream, bee's wax is melted by indirect heating at 80 degree C. and then stearic acid and glycerol monostearate are also mixed and the mixture is melted. This comprises oil phase of the cream. The aqueous phase is introduced in oil phase with stirring for 5–10 minutes, and then allowed to cool with stirring. Thus the emulsion, which has formed by mixing the two phases is brought to 25 degree C. After cooling, the emulsion becomes quite thick. Essential oils are dissolved in propylene glycol and then added in the cream with stirring.

The invention is illustrated with the help of following examples which are merely illustrative and should not be construed to limit the scope of invention.

EXAMPLE-1

| Components | Weight percentage |
| --- | --- |
| Beeswax | 4.50 |
| Stearic acid | 3.50 |
| Glycerol monostearate | 7.00 |
| Olive oil | 25.00 |
| Aloe vera gel | 11.00 |
| Rose water | 20.00 |
| Glycerine | 14.00 |
| Triethanolamine | 1.50 |
| Propylene glycol | 6.00 |
| Geranium oil | 0.50 |
| Sandalwood oil | 0.50 |
| Vetiver oil | 0.50 |
| Methyl Paraben | 0.20 |
| Propyl Paraben | 0.20 |

EXAMPLE-2

| Components | Weight % |
| --- | --- |
| Beeswax | 4.00 |
| Stearic acid | 3.50 |
| Glycerol monostearate | 6.50 |
| Olive oil | 20.00 |
| Aloe vera gel | 12.00 |
| Rose water | 25.00 |
| Glycerine | 18.00 |
| Triethnolamine | 2.00 |
| Methyl paraben | 0.15 |
| Propyl paraben | 0.15 |
| Propylene glycol | 6.00 |
| Sandalwood oil | 1.00 |
| Vetiver oil | 1.00 |
| Geranium oil | 1.00 |

EXAMPLE-3

| Components | Weight % |
| --- | --- |
| Beeswax | 4.00 |
| Stearic acid | 3.50 |
| Glycerol monostearate | 7.00 |
| Olive oil | 23.00 |
| Aloe vera gel | 11.00 |
| Rose water | 22.00 |
| Glycerine | 16.00 |
| Triethnolamine | 1.50 |
| Methyl paraben | 0.20 |
| Propyl paraben | 0.20 |
| Propylene glycol | 8.00 |
| Sandalwood oil | 1.00 |
| Vetiver oil | 1.00 |
| Geranium oil | 1.00 |

A natural herbal lotion for skin care comprising of compositions explained in the examples as given above as examples 1–3, was formulated.

Survey Report

Thirty eight persons (7 Male of 31 Female) were provided with 50 g sample of the product, along with a questionnaire for continuous use of the product for at least one week and up to a maximum period of two weeks and give feedback. The identified persons were monitored periodically for follow-up action on actual use of the product.

Compilation of the observations were categorized into six broad groups on the basis of wide spectrum applicability of the cream. In total, 71 individual test-reports were thus made available in the first week by means of simultaneous use of the product for the six categories. Similarly, 50 cases were made available with two weeks use of the product. In total, 121 were studied.

Feedback i) Acne/pimples/white & black heads: Out of 9 cases studied for one week, 44% reported moderate to high effectiveness of the cream with 33% finding no action. Rest reported slow action. A similar result was observed in 7 cases observed for two weeks, where 43% reported moderate to high effectiveness; 29% could not find any action.

ii) Dry/dehydrated skin: Out of 24 cases studied for one week, 96% responded moderate to high effectiveness with just one solitary case of "no action". All the 11 cases studied for two weeks, responded moderate to high effectiveness (100%).

iii) Cuts/wounds/burns/cracks/sunburn: Out of 14 cases studied for one week and 11 for two weeks, 79 and 82%, respectively, reported moderate to high effectiveness of the product. Number of persons reporting no action was 1 and nil in the first and second weeks, respectively.

iv) Itching of skin/unknown skin infections or eruptions: Out of five such cases studied, 80% responded moderate to high effectiveness in one week of observation. While the 1 one case using the product for two weeks reported its high effectiveness, none reported absence of any effect in the entire study.

v) Dark patches/dark circles: Out of six cases studied for one week, 67% reported moderate to high effectiveness of the cream, the rest reporting slow action. "No action" was reported by no one. Out of five cases observed for two weeks use, 80% reported moderate to high effectiveness and just one case reported slow action.

vi) Revitalization of skin/making skin soft and smooth: Out of 13 and 15 cases studied for one and two weeks, respectively, 92 and 93% reported moderate to high action. "No action" was observed in just one case out of the total 28 cases.

Observations:

i) The product was effective for nearly half of the cases when tested for acne/pimples/white and black heads. The result remained same for persons using the product for both one and two weeks.

ii) The product responds better to replenish dry and dehydrated skin (face/hands/legs). The response was 96% positive after one week's use, which was improved to 100% with two week's use.

iii) About 80% success (moderate and high effectiveness) has been achieved in curing cuts/wounds/burns etc., for both one and two week long uses. A similar observation was made for unknown skin infections.

iv) Out of 6 cases studied for one week for dark circles and patches on the face, 67% responded moderate to high effectiveness of the product. However, the response improved to 80% with two week long use.

v) Out of 13 and 15 cases studied for one and two week long use, 92% responded with reports of its effectiveness in both the cases.

vi) Out of the 38 individuals, 95% showed satisfaction over the odour and softness/smoothens of the product.

SUMMARY

The product is highly effective for dry/dehydrated skin, cuts/wounds/burns and revitalization (soft and smooth) of facial skin. It can also be used for dark patches/circles on face. Two weeks use is recommended for all such cases. The aroma of the product as one of the synergistic effects of the blended oils, has been liked by the individuals observed for study. The survey has shown an over all encouraging results.

ADVANTAGES OF THE PRESENT INVENTION

1. The product composition is safe for use topically and the components used in the formulation are of herbal origin and do not produce any adverse effect on the skin.
2. The product is ecofriendly and economically viable.
3. No harmful components are used which ultimately spoil the skin.

We claim:

1. A herbal skin care formulation comprising up to five percent of beeswax, up to four percent of stearic acid, up to seven percent of glycerol monostearate, up to thirty percent of olive oil, up to twelve percent of aloe gel, up to eighteen percent glycerine, up to two percent of triethanolamine, up to 0.2 percent of methyl paraben, up to 0.2 percent of propyl paraben, up to eight percent of propylene glycol, up to one percent of vetiver essential oil, up to one percent of geranium oil, up to one percent of sandalwood oil, and the balance comprising rose water to complete the formulation, wherein the constituents are present in terms of weight %.

2. A herbal skin care formulation according to claim 1 comprising beeswax, stearic acid, glycerol monostearate, olive oil, *Aloe vera* gel, rose water, glycerine, triethanolamine, propylene glycol, geranium oil, sandalwood oil, vetiver oil, methyl paraben and propyl paraben in amounts of 4.4–5%; 3.5–4%; 6.5–7%; 20–25%; 11–12%; 20–25% 14–18% 1.5–2%; 6–8%; 0.5–1%; 0.5–1%; 0.5–1%; 0.15–0.2% and 0.15–0.2% respectively, wherein the said constituents are expressed in terms of weight %.

3. A herbal skin care formulation as defined in claim 1 wherein said *Aloe vera* gel is obtained from flowers, leaves and stems of the *Aloe vera* plant.

4. A herbal skin care formulation as claimed in claim 1 wherein said sandalwood oil is extracted from sandalwood heartwood or soft wood.

5. A herbal skin care formulation as claimed in claim 1 wherein said vetiver oil is extracted from roots of plants.

6. A herbal skin care formulation according to claim 1 wherein said geranium oil is extracted from leaves of a plant.

7. A herbal skin care formulation according to claim 1 wherein said rose water is obtained from the distillation of rose flowers.

8. A herbal skin care formulation according to claim 1 wherein beeswax, stearic acid and glycerol monostearate form a cream base for the formulation.

9. A herbal skin care formulation as claimed in claim 1 wherein the olive oil is extracted from olive berries.

10. A herbal skin care formulation according to claim 1 comprising;

| Ingredient | Wt. % |
| --- | --- |
| Bees wax | 4.50 |
| Stearic acid | 3.50 |
| Glycerol monostearate | 7.00 |
| Olive oil | 25.00 |
| Aloe vera gel | 11.00 |
| Rose water | 20.00 |
| Glycerine | 14.00 |
| Triethanolamine | 1.50 |
| Propylene glycol | 6.00 |
| Geranium oil | 0.50 |
| Sandalwood oil | 0.50 |
| Vetiver oil | 0.50 |
| Methyl Paraben | 0.20 |
| Propyl Paraben | 0.20. |

11. A herbal skin care formulation according to claim 1 comprising;

| Ingredient | Wt. % |
| --- | --- |
| Bees wax | 4.00 |
| Stearic acid | 3.50 |
| Glycerol monostearate | 6.50 |
| Olive oil | 20.00 |
| Aloe vera gel | 12.00 |
| Rose water | 25.00 |
| Glycerine | 18.00 |
| Triethanolamine | 2.00 |
| Methyl paraben | 0.15 |
| Propyl paraben | 0.15 |
| Propylene glycol | 6.00 |
| Sandalwood oil | 1.00 |
| Vetiver oil | 1.00 |
| Geranium oil | 1.00. |

12. A herbal skin care formulation according to claim 1 comprising;

| Ingredient | Wt. % |
|---|---|
| Bees wax | 4.00 |
| Stearic acid | 3.50 |
| Glycerol monostearate | 7.00 |
| Olive oil | 23.00 |
| Aloe vera gel | 11.00 |
| Rose water | 22.00 |
| Glycerine | 16.00 |
| Triethanolamine | 1.50 |
| Methyl paraben | 0.20 |
| Propyl paraben | 0.20 |
| Propylene glycol | 8.00 |
| Sandalwood oil | 1.00 |
| Vetiver oil | 1.00 |
| Geranium oil | 1.00. |

13. A process for the preparation of a herbal skin care formulation comprising up to five percent of beeswax, up to four percent of stearic acid, up to seven percent of glycerol monostearate, up to thirty percent of olive oil, up to twelve percent of aloe gel, up to eighteen percent glycerine, up to two percent of triethanolamine, up to 0.2 percent of methyl paraben, up to 0.2 percent of propyl paraben, up to eight percent of propylene glycol, up to one percent of vetiver essential oil, up to one percent of geranium oil, up to one percent of sandalwood oil, and the balance comprising rose water to complete the formulation, the constituents being present in terms of weight %, said process comprising forming an aqueous phase by blending aloe gel with rose water and tan emulsifier, preparing an oil phase comprising beeswax, stearic acid and glycerol, introducing the aqueous phase into the oil phase under stirring to form a mixture, and then allowing the mixture to cool, dissolving the essential oils in propylene glycol and then adding the solution of essential oils to the mixture while stirring.

* * * * *